US 8,103,483 B2

(12) United States Patent
Lo et al.

(10) Patent No.: US 8,103,483 B2
(45) Date of Patent: Jan. 24, 2012

(54) ACCURATE DETECTION OF SLEEP-DISORDERED BREATHING

(75) Inventors: Men-Tzung Lo, Jhongli (TW); Yanhui Liu, Mountain View, CA (US)

(73) Assignee: DynaDx Corporation, Mountain View, CA (US)

( * ) Notice: Subject to any disclaimer, the term of this patent is extended or adjusted under 35 U.S.C. 154(b) by 697 days.

(21) Appl. No.: 12/248,024

(22) Filed: Oct. 8, 2008

(65) Prior Publication Data

US 2010/0087747 A1    Apr. 8, 2010

(51) Int. Cl.
G06F 17/14    (2006.01)
(52) U.S. Cl. .......................... 702/194; 702/179
(58) Field of Classification Search .................. None
See application file for complete search history.

(56) References Cited

U.S. PATENT DOCUMENTS

| | | | |
|---|---|---|---|
| 5,105,354 A | 4/1992 | Nishimura | |
| 5,902,250 A | 5/1999 | Verrier | |
| 6,375,623 B1* | 4/2002 | Gavriely | 600/534 |
| 6,415,174 B1 | 7/2002 | Bebehani | |
| 6,738,734 B1* | 5/2004 | Huang | 702/194 |
| 7,324,845 B2 | 1/2008 | Mietus | |
| 2003/0033094 A1* | 2/2003 | Huang | 702/39 |
| 2003/0045806 A1* | 3/2003 | Brydon | 600/534 |
| 2003/0055348 A1* | 3/2003 | Chazal et al. | 600/509 |
| 2005/0020930 A1* | 1/2005 | Salisbury et al. | 600/529 |
| 2007/0032733 A1* | 2/2007 | Burton | 600/509 |
| 2007/0287923 A1* | 12/2007 | Adkins et al. | 600/485 |
| 2008/0287815 A1* | 11/2008 | Chon et al. | 600/507 |

OTHER PUBLICATIONS

Chappell and Payne (2005) Annals of Biomed Eng vol. 33(10): 1411-1421.*

* cited by examiner

*Primary Examiner* — N. C. Yang
*Assistant Examiner* — Richard Moerschell
(74) *Attorney, Agent, or Firm* — SV Patent Service

(57) ABSTRACT

A method for detecting sleep-disordered breathing (SDB) includes acquiring a time sequence of a physiological signal from an individual, wherein the time sequence of the physiological signal includes a oscillatory pattern, computing an oscillatory interval signal using the time sequence of the physiological signal, decomposing the oscillatory interval signal into a plurality of ensemble empirical modes, selecting one of the plurality of ensemble empirical modes, calculating at least one of average amplitude or standard deviation of the instantaneous frequency in the selected ensemble empirical mode; and identifying SDB using at least one of the average amplitude or the standard deviation of the instantaneous frequency.

23 Claims, 6 Drawing Sheets

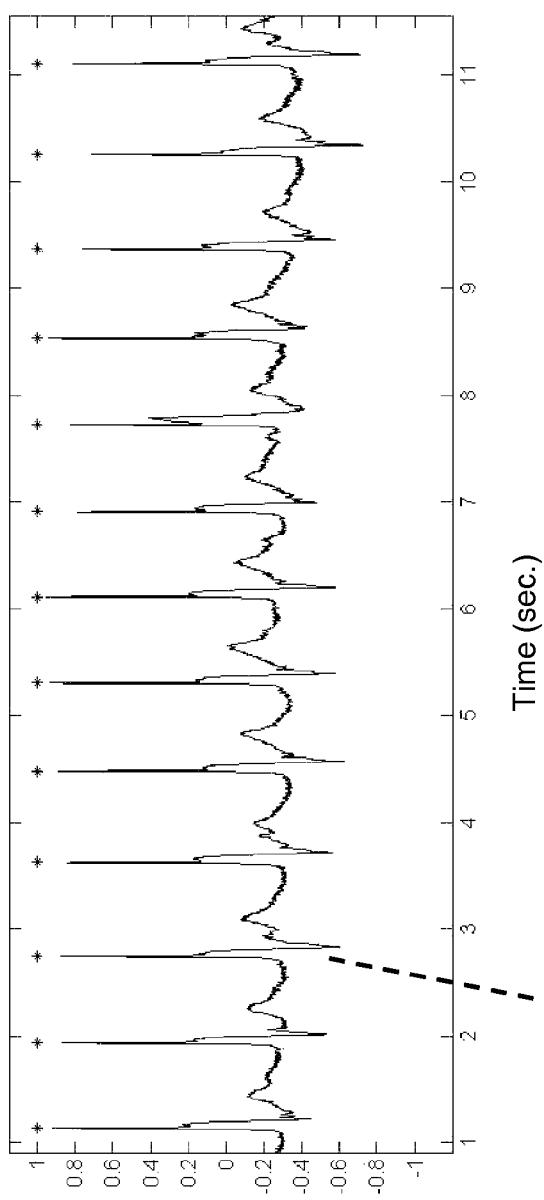
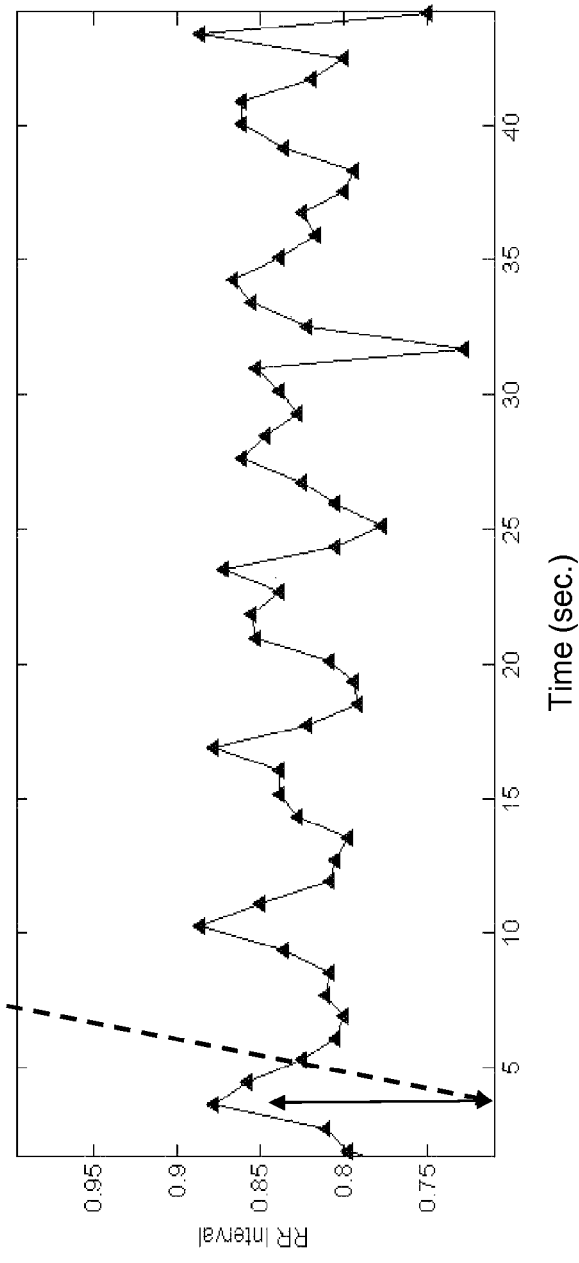
Fig. 3A
Fig. 3B

ACCURATE DETECTION OF SLEEP-DISORDERED BREATHING

BACKGROUND

The present disclosure relates generally to diagnosing sleep-disordered breathing (SDB) non-invasively by analyzing physiologic data.

Sleep-disordered breathing (SDB) describes a group of respiratory disorder during sleep. Obstructive sleep apnea (OSA), the most common such disorder, is characterized by periodic cessations of breathing during sleep due to intermittent airway obstructions. OSA is a frequently undiagnosed condition affecting millions of individuals worldwide, and it is associated with increased morbidity and mortality.

Conventional diagnosis technologies for sleep-disordered breathing require overnight monitoring of a patient in a specially equipped sleep laboratory. Standard polysomnographic recordings in a sleep laboratory typically include electro-encephalography (EEG), electro-oculography (EOG), electromyography (EMG), airflow, respiratory efforts, $SpO_2$, body position, and electrocardiography (ECG), which are often expensive and inconvenient to use. Less costly, easier or home-based, and reliable techniques are therefore desirable for detecting SDB in high-risk population.

SUMMARY

In a general aspect, the present invention relates to a method for detecting sleep-disordered breathing (SDB). The method includes acquiring a time sequence of a physiological signal from an individual, wherein the time sequence of the physiological signal includes a oscillatory pattern; computing an oscillatory interval signal using the time sequence of the physiological signal; decomposing the oscillatory interval signal into a plurality of ensemble empirical modes; selecting one of the plurality of ensemble empirical modes; calculating at least one of average amplitude or standard deviation of the instantaneous frequency in the selected ensemble empirical mode; and identifying SDB using at least one of the average amplitude or the standard deviation of the instantaneous frequency.

In another general aspect, the present invention relates to a method for detecting sleep-disordered breathing (SDB). The method includes acquiring a first time sequence of a first physiological signal from an individual, wherein the first time sequence of the first physiological signal includes a first oscillatory pattern; computing a first oscillatory interval signal using the first time sequence of the first physiological signal; decomposing the first oscillatory interval signal into a first group of ensemble empirical modes; calculating a first amplitude-frequency characteristics in one of the first group of ensemble empirical mode; acquiring a second time sequence of a second physiological signal from an individual, wherein the second time sequence of the second physiological signal includes a second oscillatory pattern; computing a second oscillatory interval signal using the second time sequence of the second physiological signal; decomposing the second oscillatory interval signal into a second group of ensemble empirical modes; calculating a second amplitude-frequency characteristics in one of the second group of ensemble empirical mode; and identifying SDB using at least one of the first amplitude-frequency characteristics or the second amplitude-frequency characteristics.

In another general aspect, the present invention relates to a computer program product comprising a computer useable medium having computer readable program code functions embedded in said medium for causing a computer to acquire a time sequence of a physiological signal from an individual, wherein the time sequence of the physiological signal includes a oscillatory pattern; compute an oscillatory interval signal using the time sequence of the physiological signal; decompose the oscillatory interval signal into a plurality of ensemble empirical modes; select one of the plurality of ensemble empirical modes; calculate at least one of average amplitude or standard deviation of the instantaneous frequency in the selected ensemble empirical mode; and identifying sleep-disordered breathing (SDB) using the average amplitude and the standard deviation of the instantaneous frequency.

In another general aspect, the present invention relates to a system for detecting sleep-disordered breathing (SDB). The system includes a probe configured to acquire a time sequence of a physiological signal from an individual, wherein the time sequence of the physiological signal includes a oscillatory pattern; and an analyzer configured to compute oscillatory interval signal using the time sequence of the physiological signal, to decompose the oscillatory interval signal into a plurality of ensemble empirical modes, to calculate at least one of average amplitude or standard deviation of the instantaneous frequency in one of the plurality of ensemble empirical modes, and to identify SDB using the average amplitude and the standard deviation of the instantaneous frequency.

Implementations of the system may include one or more of the following. The oscillatory pattern in the time sequence of the physiological signal can include a plurality of repetitive peaks, wherein the step of computing oscillatory interval signal can include computing distances between the repetitive peaks. The step of decomposing can include obtaining an envelope of local maxima and local minima in the oscillatory interval signal to obtain a first mode in the plurality of ensemble empirical modes; and subtracting the first mode from the oscillatory interval signal to obtain a second mode in the plurality of ensemble empirical modes. The selected ensemble empirical mode can include intrinsic mode fluctuations, wherein the step of calculating at least one of average amplitude and standard deviation of the instantaneous frequency can include segmenting a time sequence in the intrinsic mode fluctuations in the selected ensemble empirical mode into a plurality of segments; and calculating at least one of average amplitude or standard deviation of the instantaneous frequency in each of the plurality of segments. The step of identifying SDB can include comparing at least one of the average amplitude and the standard deviation of the instantaneous frequency with a predetermined threshold. The method can further include positively diagnosing SDB in the individual if the average amplitude exceeds the predetermined threshold. The method can further include positively diagnosing SDB in the individual if the standard deviation of the instantaneous frequency falls below the predetermined threshold. The step of calculating at least one of average amplitude or standard deviation of the instantaneous frequency can include calculating both average amplitude and standard deviation of the instantaneous frequency in the selected ensemble empirical mode. The step of identifying SDB can include comparing the average amplitude with a first predetermined threshold; and comparing the standard deviation of the instantaneous frequency with a second predetermined threshold. The method can further include positively diagnosing SDB in the individual if the average amplitude exceeds the first predetermined threshold and the standard deviation of the instantaneous frequency falls below the second predetermined threshold. The step of identifying SDB can include computing an anti-correlation between the average amplitude and the standard deviation of the instantaneous frequency in the selected ensemble empirical mode; and positively diagnosing SDB in the individual if the anti-correlation exceeds predetermined threshold. The plurality of ensemble empirical modes can include at least six modes, wherein the selected ensemble empirical mode is the sixth mode in the plurality of ensemble empirical modes. The step of selecting can include selecting one of the plurality of ensemble empirical modes that has cyclic variations having a frequency between about 0.01 Hz and about 0.1 Hz. The physiological signal can include a respiratory signal, an oxygen signal, or a cardio signal. The cardio signal can include an electrocardiography (ECG) signal.

The described systems and methods provide more reliable and more accurate detection of sleep-disordered breathing. The disclosed methods are non-invasive and are simpler and less expensive than conventional techniques.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 3A illustrates an exemplified physiological signal measured from a patient.

FIG. 3B illustrates a time sequence of a repeat interval signal calculated from the physiological signal shown in FIG. 3A.

DETAILED DESCRIPTION

Figure 1:
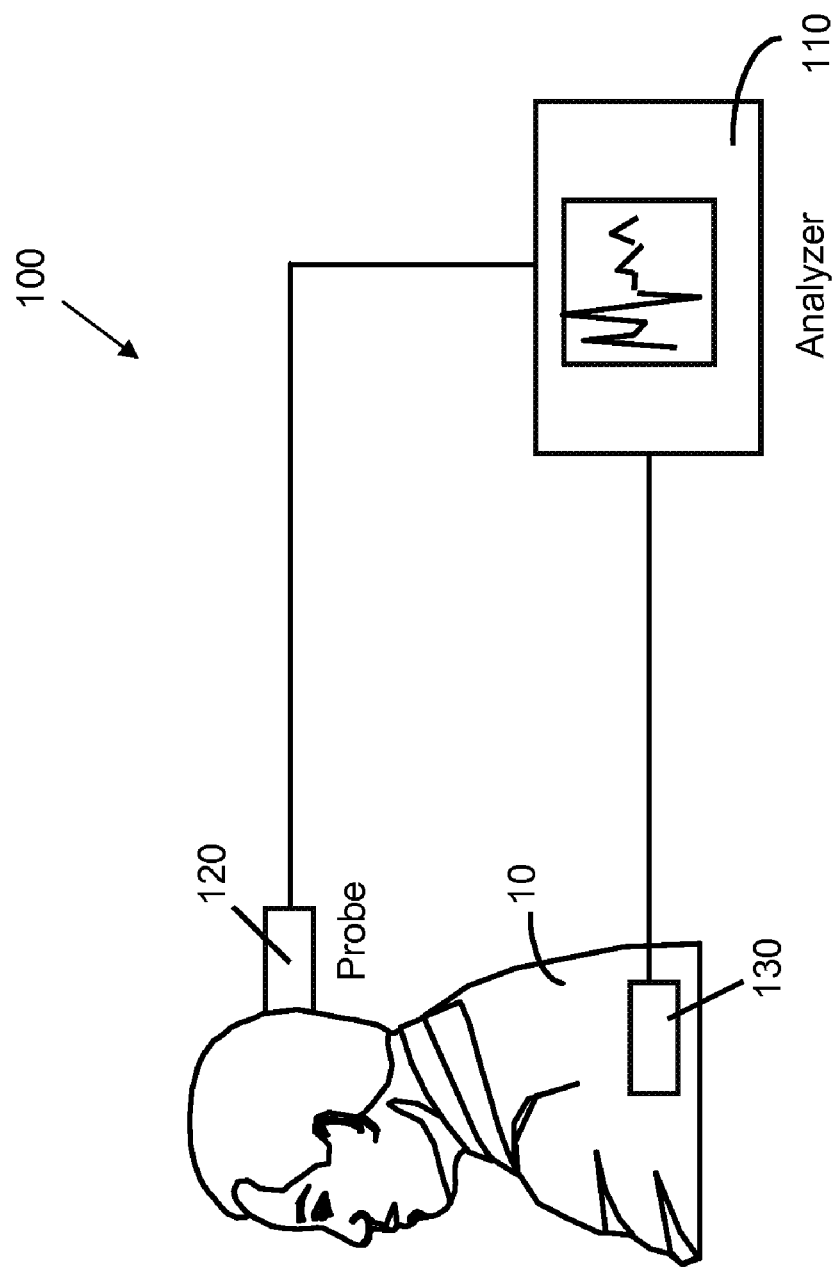
FIG. 1 is a schematic diagram illustrating a system for detecting sleep-disordered breathing.

Referring to FIG. 1, an exemplified SDB detection system 100 includes an analyzer 110 and one or more probes 120, 130 that can be attached to a patient 10. The probes 120, 130 include transducers and sensors that are configured to measure physiological signals from the patient 10 and send corresponding sensing signals to the analyzer 110. The physiological signals can include respiratory and cardio signals such as electrocardiography. The analyzer 110 can include an analog-to-digital (A/D) converter for digitizing the sensing signals which are typically in analog form. The analyzer 110 also includes a computer processor that is configured to process and analyze the sensing signals after they are digitized by the A/D converter. An algorithm can be pre-stored in a computer memory in the analyzer 110 for analyzing the sensing signals. The analyzer 110 can also include necessary input/output devices that allow a user to enter instructions to process the data, and a display for displaying the raw sensing signals and data calculated from the sensing signals. One or more of the analyzing steps described below can be automated. As described below the detection of the SDB pattern can be fully automated.

Figure 2:
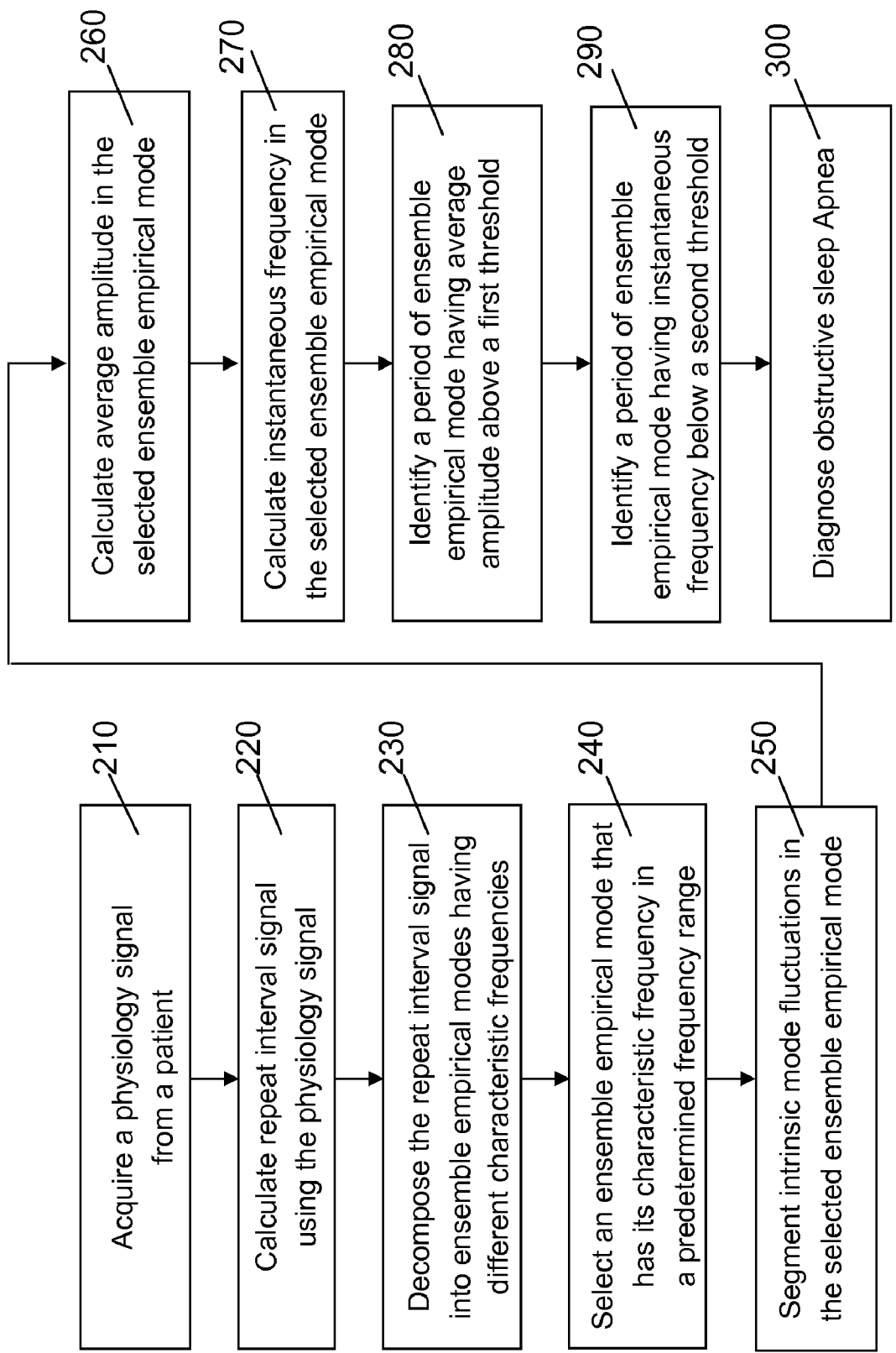
FIG. 2 is a flow diagram illustrating the steps of detecting sleep-disordered breathing.

The SDB detection, referring to FIG. 2, can include one or more of the following steps. Physiological signals are first acquired (step 210) from an individual using the SDB detection system 100 (shown in FIG. 1). The physiological signals can include respiratory and cardio signals such as ECG. For example, an example of an ECG signal obtained from the individual is shown in FIG. 3A. The ECG signal shows typical oscillatory pattern (or repeat pattern) caused by the breathing of the individual. The ECG signal includes a sequence of repetitive peaks separated by intervals.

Repeat interval signals, shown in FIG. 3B, are next calculated from the ECG signal (step 220). The calculation of each repeat interval value in the repeat interval signal (also referred as RR signal) by measuring the distance between adjacent peaks in the ECG signal. The repeat interval signal has a non-stationary pattern, which can include quasi-periodic patterns at different frequencies.

Figure 4A:
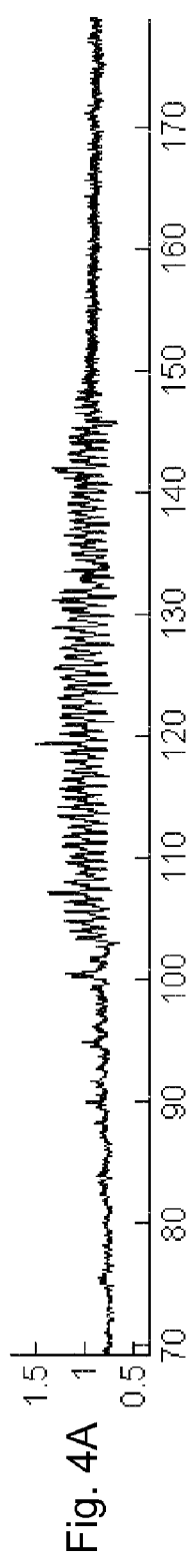
FIG. 4A illustrates a time sequence of a repeat interval signal showing SDB behavior in a patient.

FIG. 4A illustrates a time sequence of a repeat interval signal showing SDB behavior in a patient. In the background of signals characterized by quasi-periodic patterns, the repeat interval signal includes a period of time in which the oscillation dynamics have significantly higher amplitudes than those in the background. The repeat interval value in this period varies much more than in the background times. The ECG signal in this period is characterized by cyclic increases and decreases associated with the apneic phase and the resumption of breathing, which is often related to prolonged SDB.

The cyclic variations in a frequency range between 0.01 Hz and 0.1 Hz are a distinctive feature for SDB that is not found during normal respiration. The repeat interval signal therefore needs to be decomposed to single out the oscillatory behavior between 0.01 Hz and 0.1 Hz. Since repeat interval signals from an ECG signal (or other physiological signals such as respiratory rhythm) are non-stationary signals in which the target SDB behavior is prominent and of high density only for a period of time, Fourier transform is not an effective approach to filter out the target signals. Instead, the repeat interval signal is decomposed into ensemble empirical modes having different characteristic frequencies (step 230 in FIG. 2).

Figure 4B:
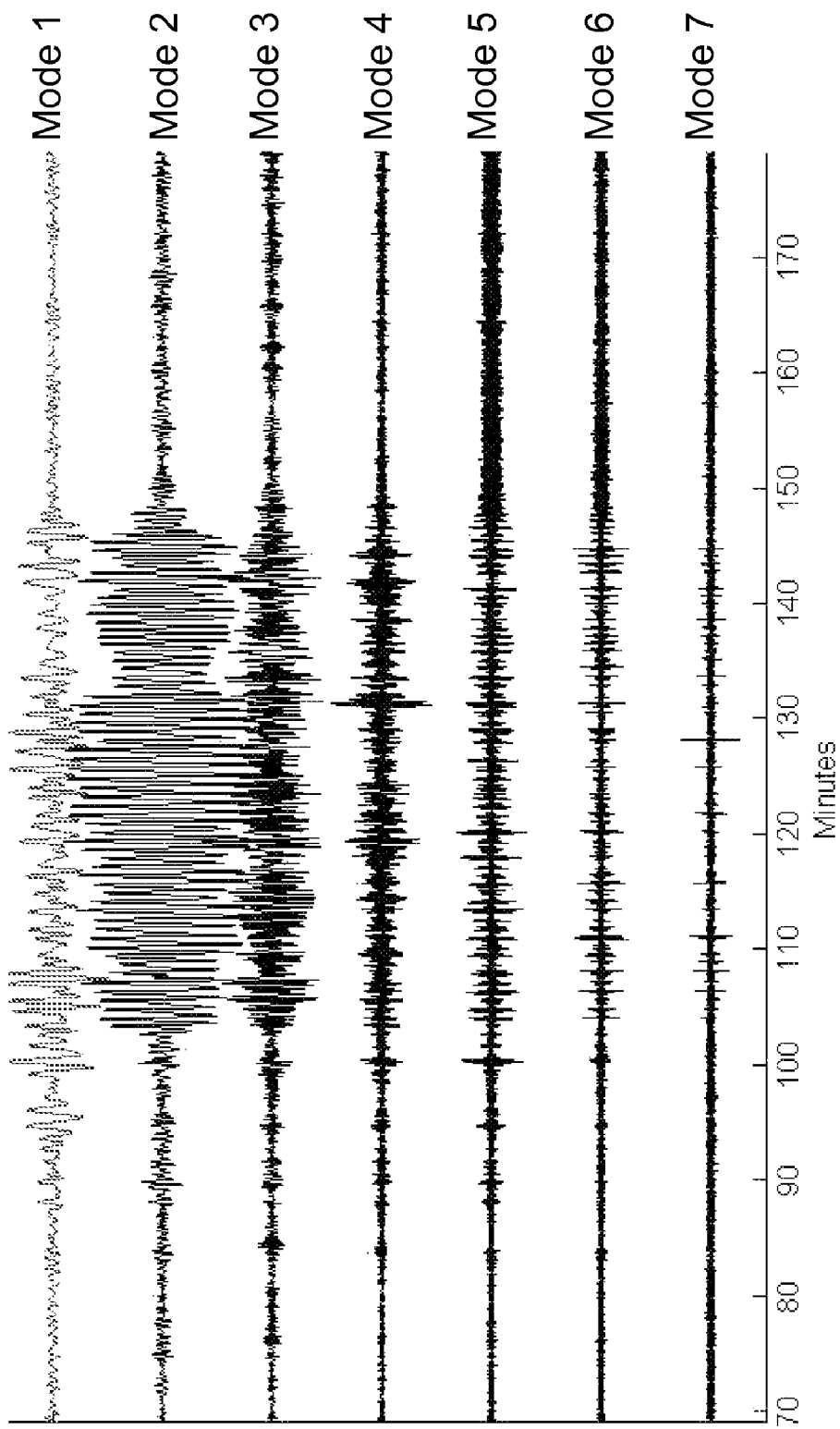
FIG. 4B illustrates a time sequences of intrinsic mode signals calculated from the repeat interval signal in FIG. 4A.

Referring to FIG. 4B, the repeat interval signal in FIG. 4A is decomposed into several ensemble empirical modes: Mode 1 to Mode 7, each of which is characterized by intrinsic mode fluctuations. Mode 1 is obtained by tracing the envelope of local maxima and local minima in the repeat interval signal. Mode 1 is then subtracted from the repeat interval signal to obtain a first residual signal. Mode 2 is obtained by tracing the envelope of the maxima and minima in the first residual signal. Mode 2 is then subtracted from the first residual signal to obtain a second residual signal. Mode 3 is similarly calculated from the second residual signal. The above described decomposition procedure leads to decreased oscillation frequencies from Mode 1 to Mode 7 in the intrinsic mode fluctuations. Successive decomposition steps can decrease typical oscillation frequencies approximately by a factor of two.

The intrinsic mode fluctuations in an ensemble empirical mode represent a frequency-amplitude modulation in a narrow band, which can be related to specific physiology process. An ensemble empirical mode that has its characteristic frequency in a predetermined frequency range is next selected (step 240 in FIG. 2). For instance, if the behavior between 0.01 Hz and 0.1 Hz is of interest for detecting SDB behavior, an ensemble empirical mode that has its associated characteristic frequency in this frequency range is selected. For example, Mode 6 in FIG. 4B (and re-plotted in more detail in FIG. 5A) is selected for further analysis because its characteristic frequency falls into this frequency range.

In accordance to the present invention, SDB can be determined by analyzing one or more amplitude-frequency characteristics of the intrinsic mode fluctuations in the selected mode. Examples of the amplitude-frequency characteristics include average amplitude and the standard deviation of the instantaneous frequency of the intrinsic mode fluctuations.

Figure 5A:
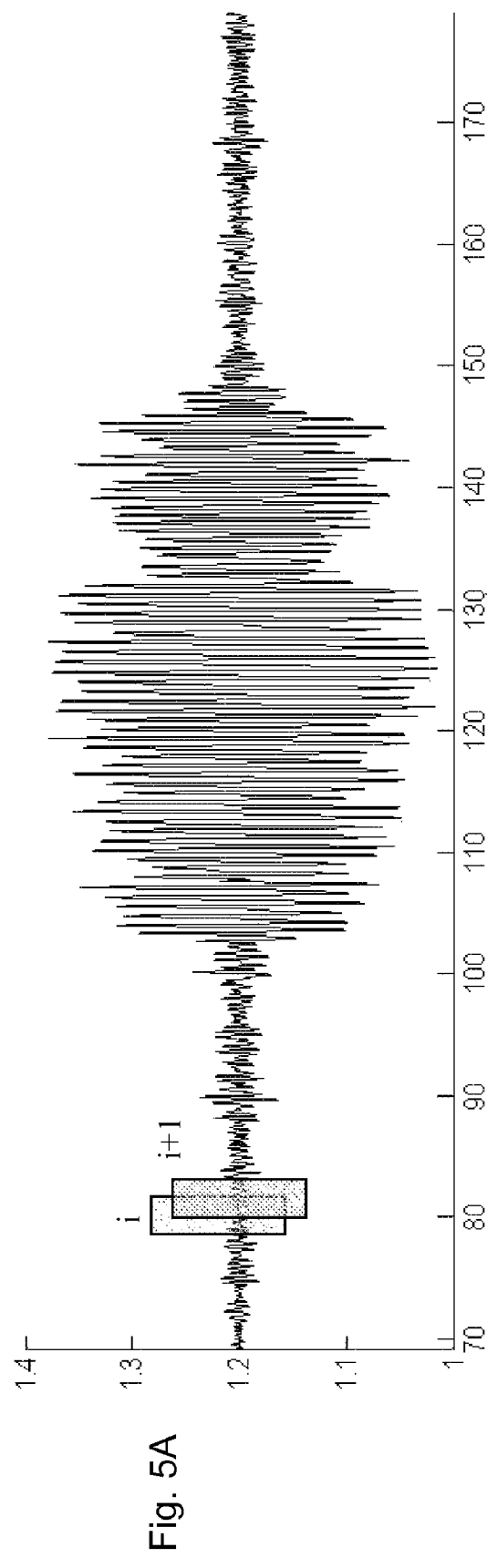
FIG. 5A illustrates segmentations of one of the intrinsic mode signals shown in FIG. 4B.

To calculate the amplitude-frequency characteristics, the intrinsic mode fluctuations in Mode 6 are first segmented to prepare for analysis (step 250 in FIG. 2). As shown in FIG. 5A, the intrinsic mode fluctuations in Mode 6 is divided into overlapped segments such as ith and (i+1)th segments. The average amplitude in each segment is computed by applying Hilbert transform to the intrinsic mode fluctuations in the segment, which results in an amplitude value in the selected ensemble empirical mode (step 260 in FIG. 2). The sampling segment may be, for example, approximately 5-6 min long. The next sampling segment is shifted from the first sampling segment by an incremental step (such as 30 second). The same steps are repeated to calculating the average amplitude. The incremental steps between successive sampling segments are typically kept constant. A time sequence of the average amplitude of the intrinsic mode fluctuations in the selected mode (i.e. Mode 6) is plotted in FIG. 5B.

Similarly, the standard deviation of the instantaneous frequency in each above described segment is computed by applying Hilbert transform to the intrinsic mode fluctuations in the segment, which results in a standard deviation value in the selected ensemble empirical mode (step 270 in FIG. 2). A time sequence of the standard deviation of the instantaneous frequency of the intrinsic mode fluctuations in the selected mode (i.e. Mode 6) is plotted in FIG. 5C.

Figure 5B:
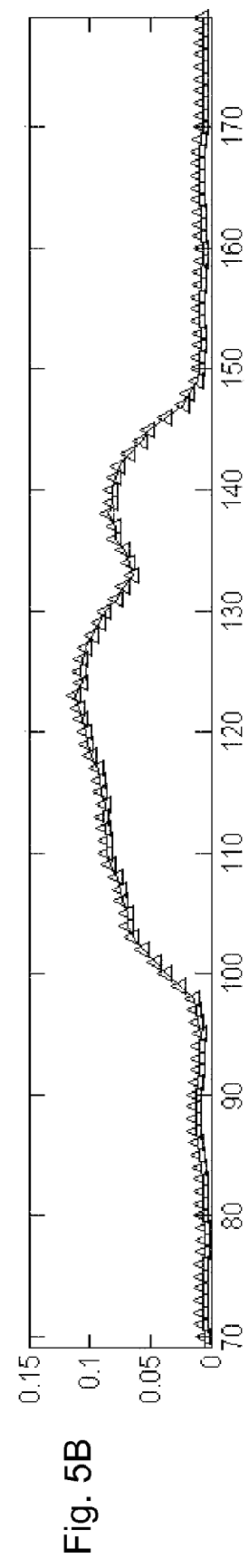
FIG. 5B illustrates a time sequence of average amplitude calculated by the segmentation of the intrinsic mode signal as shown in FIG. 5A.

As shown in FIG. 5B, the average amplitude of the intrinsic mode fluctuations in the selected ensemble empirical mode is larger in the segment related to SDB behavior (as shown in the range between 100 minutes and 145 minutes in FIG. 5B), which indicates prominent non-periodic heart-beat pattern in the ECG signal during the SDB period. Normal heart beat, on the other hand, is characterized by small amplitude in selected ensemble empirical mode, which corresponds to non-periodic pattern in the ECG signal. In accordance with the present invention, a first threshold for the average amplitude may be pre-stored in the SDB detection algorithm. A period of intrinsic mode fluctuations having average amplitude above the first threshold can be determined for identifying SDB behavior (step 280 in FIG. 2). The first (and the second) threshold can be obtained by studies from historic clinical data. For example, SDB can be diagnosed if the average amplitude exceeds a threshold of 0.06 in FIG. 5B.

Figure 5C:
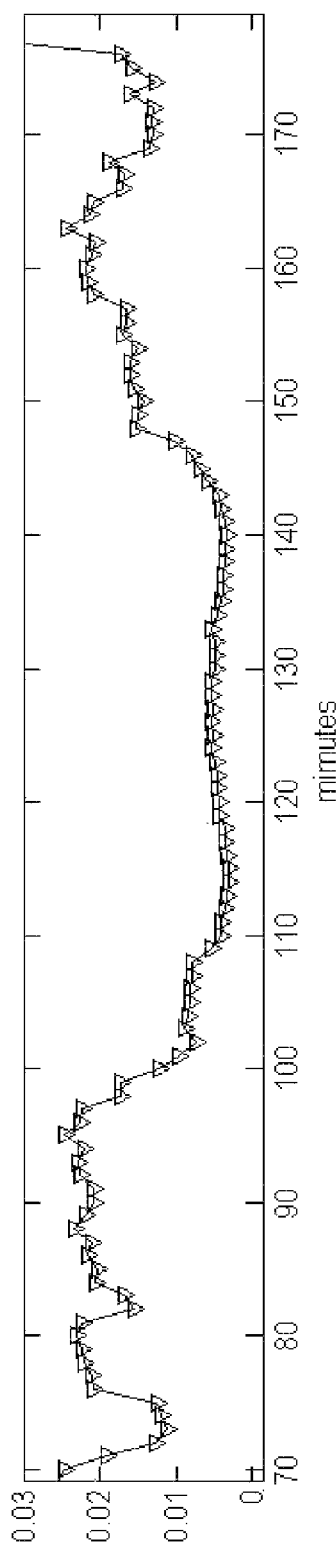
FIG. 5C illustrates a time sequence of the standard deviation of the instantaneous frequency of the intrinsic mode fluctuations of the intrinsic mode signal as shown in FIG. 5A.

Similarly, referring to FIG. 5C, the standard deviation of the instantaneous frequency of the intrinsic mode fluctuations in the selected ensemble empirical mode is shown to be fluctuated a lot for different segments. The standard deviation of the instantaneous frequency is drastically reduced in the epoch related to SDB behavior (i.e. in the range between 100 minutes and 145 minutes in FIG. 5C). A second threshold for the standard deviation of the instantaneous frequency may be pre-stored in the SDB detection algorithm. A period of intrinsic mode fluctuations having the standard deviation of the instantaneous frequency below the pre-determined threshold can be determined for identifying SDB behavior (step 290 in FIG. 2). For example, SDB can be diagnosed if the standard deviation of the instantaneous frequency falls below a threshold of 0.01 in FIG. 5C.

Sleep-disordered breathing can be identified (step 300 in FIG. 2) either when the average amplitude exceeds its associated threshold value, or when the standard deviation of the instantaneous frequency falls below its associated threshold, or when both conditions are met. Instructions for the exemplified process illustrated in FIG. 2 can be stored in a computer useable medium in a computer program product such as the analyzer 10. The computer useable medium stores a computer readable program code functions embedded in said medium for causing a computer or the SDB detection system 100 to perform the steps in FIG. 2.

In some embodiments, the average amplitude and the standard deviation of the instantaneous frequency can be cross-correlated or anti-correlated. The average amplitude and the standard deviation of the instantaneous frequency of the intrinsic mode fluctuations can be inversely correlated in the period showing SDB behavior. For example, as shown in FIGS. 5B and 5C, the average amplitude increase above average and the standard deviation of the instantaneous frequency decreases below average during the SDB period. The inverse of the standard deviation of the instantaneous frequency can be correlated with the average amplitude. SDB can be identified if such anti-correlation between the average amplitude and the standard deviation of the instantaneous frequency exceeds a pre-determined threshold.

Figure 6:
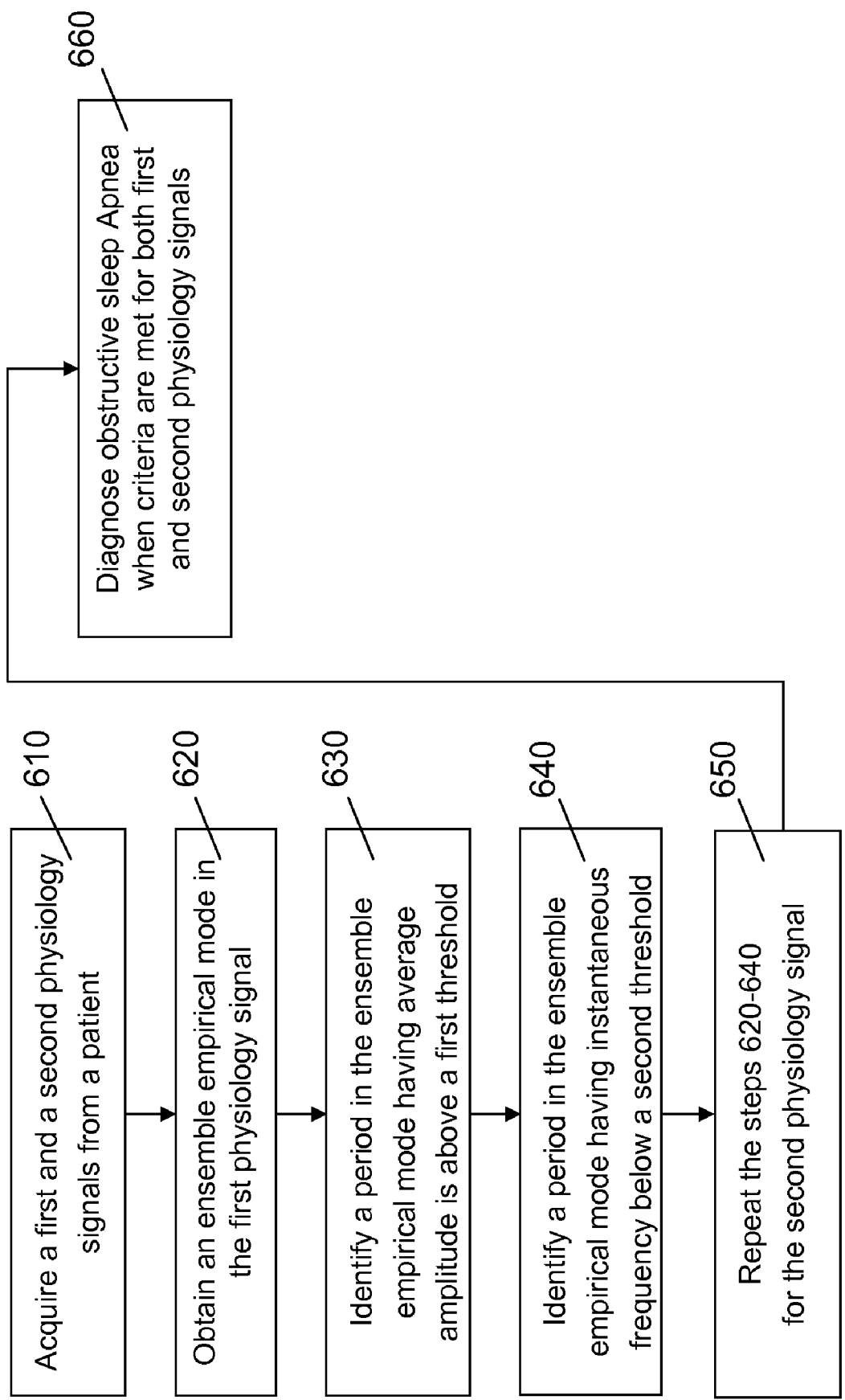
FIG. 6 is a flow diagram illustrating another process for detecting sleep-disordered breathing.

In some embodiments, referring to FIG. 6, a plurality of physiological signals can be obtained from a patient (step 610). For example, a first physiological signal can be related to breathing. A second physiological signal can be related to cardio activities. An ensemble empirical mode can be calculated and selected in the first physiological signal using steps illustrated FIG. 2 (step 620). The average amplitude and the standard deviation of the instantaneous frequency are then calculated in the first physiological signal and compared with their respective threshold values (steps 630 and 640). Similarly, the average amplitude and the standard deviation of the instantaneous frequency are then calculated in the second physiological signal and compared with their respective threshold values (steps 650). Sleep-disordered breathing can be identified can be diagnosed (step 660) when average amplitudes in both physiological signals exceed their respective threshold values, or when standard deviation of the instantaneous frequencies in both physiological signals fall below their respective threshold values, or when both criteria are met.

It should be understood that the described that the above described systems and methods are applicable to different physiological signals from the ones described above. For example, the physiological signals can be derived from an oxygen signal. SDB can be determined by analyzing a single physiological signal, or a combination of two, three, or more physiological signals. The frequency range for SDB described above is meant to be an example; the disclosed systems and methods are compatible with different frequency ranges.

What is claimed is:

1. A method for detecting sleep-disordered breathing (SDB), comprising:
   acquiring a time sequence of a physiological signal from an individual, wherein the time sequence of the physiological signal includes an oscillatory pattern;
   computing an oscillatory interval signal using the time sequence of the physiological signal;
   decomposing the oscillatory interval signal into a plurality of ensemble empirical modes;
   selecting one of the plurality of ensemble empirical modes to obtain a selected ensemble empirical mode comprising a time sequence of intrinsic mode fluctuations;
   segmenting the selected ensemble empirical mode into a plurality of segments;
   calculating a standard deviation of an instantaneous frequency in each of the plurality of segments in the selected ensemble empirical mode; and
   identifying SDB by comparing the standard deviations of the instantaneous frequencies in the selected ensemble empirical mode to a predetermined value.

2. The method of claim 1, wherein the oscillatory pattern in the time sequence of the physiological signal includes a plurality of repetitive peaks, wherein the step of computing oscillatory interval signal comprises computing distances between the repetitive peaks.

3. The method of claim 1, wherein the step of decomposing comprises:
   obtaining an envelope of local maxima and local minima in the oscillatory interval signal to obtain a first mode in the plurality of ensemble empirical modes; and
   subtracting the first mode from the oscillatory interval signal to obtain a second mode in the plurality of ensemble empirical modes.

4. The method of claim 1, wherein at least one of the plurality of segments has a width in a range between 5 minutes and 6 minutes.

5. The method of claim 1, wherein the step of identifying SDB comprises:
   comparing the standard deviation of the instantaneous frequency with a predetermined threshold.

6. The method of claim 1, wherein successive segments in the plurality of segments are shifted by an incremental step and overlap with each other.

7. The method of claim 5, further comprising positively diagnosing SDB in the individual if the standard deviation of the instantaneous frequency falls below the predetermined threshold.

8. The method of claim 1, further comprising: calculating an average amplitude in each of the plurality of segments in the selected ensemble empirical mode.

9. The method of claim 8, wherein the step of identifying SDB comprises:
   comparing the average amplitude with a first predetermined threshold; and
   comparing the standard deviation of the instantaneous frequency with a second predetermined threshold.

10. The method of claim 9, further comprising positively diagnosing SDB in the individual if the average amplitude exceeds the first predetermined threshold and the standard deviation of the instantaneous frequency falls below the second predetermined threshold.

11. The method of claim 8, wherein the step of identifying SDB comprises:
   computing an anti-correlation between the average amplitude and the standard deviation of the instantaneous frequency in the selected ensemble empirical mode; and
   positively diagnosing SDB in the individual if the anti-correlation exceeds predetermined threshold.

12. The method of claim 1, wherein the plurality of ensemble empirical modes comprises at least six modes, wherein the selected ensemble empirical mode is the sixth mode in the plurality of ensemble empirical modes.

13. The method of claim 1, wherein the step of selecting comprises selecting one of the plurality of ensemble empirical modes that has cyclic variations having a frequency between about 0.01 Hz and about 0.1 Hz.

14. The method of claim 1, wherein the physiological signal comprises a respiratory signal, an oxygen signal, or a cardio signal.

15. The method of claim 14, wherein the cardio signal comprises an electrocardiography (ECG) signal.

16. A method for detecting sleep-disordered breathing (SDB), comprising:
   acquiring a time sequence of a physiological signal from an individual, wherein the time sequence of the physiological signal includes an oscillatory pattern;
   computing an oscillatory interval signal using the time sequence of the physiological signal;
   decomposing the oscillatory interval signal into a plurality of ensemble empirical modes;
   selecting one of the plurality of ensemble empirical modes to obtain a selected ensemble empirical mode comprising a time sequence of intrinsic mode fluctuations;
   segmenting the selected ensemble empirical mode into a plurality of segments;
   calculating an average amplitude in each of the plurality of segments in the selected ensemble empirical mode; and
   identifying SDB by comparing the average amplitudes in the selected ensemble empirical mode to a predetermined value.

17. The method of claim 16, wherein the oscillatory pattern in the time sequence of the physiological signal includes a plurality of repetitive peaks, wherein the step of computing oscillatory interval signal comprises computing distances between the repetitive peaks.

18. The method of claim 16, wherein the step of decomposing comprises:
   obtaining an envelope of local maxima and local minima in the oscillatory interval signal to obtain a first mode in the plurality of ensemble empirical modes; and
   subtracting the first mode from the oscillatory interval signal to obtain a second mode in the plurality of ensemble empirical modes.

19. The method of claim 16, wherein successive segments in the plurality of segments are shifted by an incremental step and overlap with each other.

20. The method of claim 16, wherein the step of identifying SDB comprises:
   comparing the average amplitude with a predetermined threshold; and
   positively diagnosing SDB in the individual if the average amplitude exceeds the predetermined threshold.

21. The method of claim 16, wherein the plurality of ensemble empirical modes comprises at least six modes, wherein the selected ensemble empirical mode is the sixth mode in the plurality of ensemble empirical modes.

22. The method of claim 16, wherein the physiological signal comprises a respiratory signal, an oxygen signal, a cardio signal, or an electrocardiography (ECG) signal.

23. The method of claim 16, further comprising:
   calculating a standard deviation of an instantaneous frequency in each of the plurality of segments in the selected ensemble empirical mode; and
   diagnosing SDB in the individual using the average amplitudes and the standard deviations of the instantaneous frequencies in the selected ensemble empirical mode.

* * * * *